(12) United States Patent
Fukuda et al.

(10) Patent No.: US 10,800,800 B2
(45) Date of Patent: Oct. 13, 2020

(54) COMPOSITION, THERMOPLASTIC RESIN COMPOSITION CONTAINING THE SAME, AND MOLDED ARTICLE THEREOF

(71) Applicant: ADEKA CORPORATION, Tokyo (JP)

(72) Inventors: Takuya Fukuda, Saitama (JP); Yuri Yokota, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 16/649,428

(22) PCT Filed: Aug. 29, 2019

(86) PCT No.: PCT/JP2019/033854
§ 371 (c)(1),
(2) Date: Mar. 20, 2020

(87) PCT Pub. No.: WO2020/045554
PCT Pub. Date: Mar. 5, 2020

(65) Prior Publication Data
US 2020/0283460 A1    Sep. 10, 2020

(30) Foreign Application Priority Data

Aug. 30, 2018  (JP) .................................. 2018-162147
Dec. 5, 2018  (JP) .................................. 2018-228135

(51) Int. Cl.
*C07F 9/655* (2006.01)
*C07C 53/126* (2006.01)
*C08K 13/02* (2006.01)

(52) U.S. Cl.
CPC ............ *C07F 9/655* (2013.01); *C07C 53/126* (2013.01); *C08K 13/02* (2013.01); *C08K 2201/014* (2013.01)

(58) Field of Classification Search
CPC ....... C07F 9/655; C07C 53/126; C08K 13/02; C08K 2201/014
USPC ....................................................... 524/141
See application file for complete search history.

(56) References Cited

U.S. PATENT DOCUMENTS

| 5,342,868 A | 8/1994 | Kimura et al. |
| 2005/0197456 A1 | 9/2005 | Nicolini et al. |
| 2007/0054996 A1* | 3/2007 | Tobita .................. C08K 5/0091 524/107 |

(Continued)

FOREIGN PATENT DOCUMENTS

| CN | 101265347 A | 9/2008 |
| CN | 101845171 A | 9/2010 |

(Continued)

OTHER PUBLICATIONS

Chinese Office Action and Search Report for Chinese Application No. 201980002959.X, dated May 21, 2020.
Ren et al., "Effects of organic phosphate salt and carboxylic acid salt combined nucleating agent on properties of isotactic polypropylene," Acta Materiae Compositae Sinica, vol. 33, No. 9, 2016, pp. 2006-2012, 7 pages total, with an English abstract.
Zhang et al., "Isothermal Crystallization of Isotactic Polypropylene Nucleated with a Novel Aromatic Heterocyclic Phosphate Nucleating Agent," Journal of Macromolecular Science®, Part B: Physics, vol. 56, Nos. 11-12, 2017, pp. 811-820, 11 pages total.

(Continued)

*Primary Examiner* — Doris L Lee
(74) *Attorney, Agent, or Firm* — Birch, Stewart, Kolasch & Birch, LLP

(57) ABSTRACT

Provided are: a composition capable of imparting excellent transparency and physical properties to thermoplastic resins; a thermoplastic resin composition containing the composition; and a molded article of the thermoplastic resin composition. The composition contains the following (A), (B), (C) and (D), and ratios of respective components with respect to a total amount of (A) to (D) are: (A) 35 to 75% by mass, (B) 10 to 40% by mass, (C) 0 to 20% by mass, and (D) 5 to 35% by mass. The (A) is an aromatic phosphate metal salt represented by the following Formula (1) wherein, $R^1$ to $R^4$ each independently represent a hydrogen atom or the like; $R^5$ represents an alkylidene group having 1 to 4 carbon atoms; m represents a number of 1 or 2; when m is 1, $M^1$ represents lithium; and when m is 2, $M^1$ represents hydroxyaluminum, the (B) is a sodium carboxylate, the (C) is a fatty acid metal salt represented by the following Formula (2) wherein, $R^6$ represents a group introduced to an aliphatic organic acid having 10 to 30 carbon atoms; $M^2$ represents an n-valent metal atom or the like; and n represents an integer of 1 to 3, and the (D) is a fatty acid.

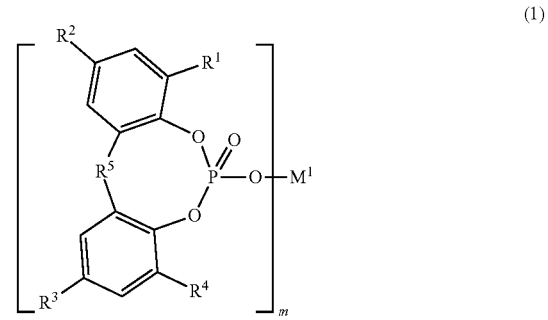

(1)

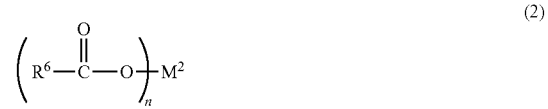

(2)

10 Claims, No Drawings

(56) References Cited

U.S. PATENT DOCUMENTS

| | | | |
|---|---|---|---|
| 2009/0156744 A1* | 6/2009 | Ishii | C08K 5/098 525/150 |
| 2012/0190797 A1 | 7/2012 | Kristiansen et al. | |
| 2013/0037743 A1* | 2/2013 | Zhao | C08L 23/12 252/182.14 |
| 2015/0096918 A1 | 4/2015 | Maeda et al. | |
| 2018/0072931 A1 | 3/2018 | Cui et al. | |

FOREIGN PATENT DOCUMENTS

| | | |
|---|---|---|
| CN | 102344609 A | 2/2012 |
| JP | 5-156078 A | 6/1993 |
| JP | 8-120116 A | 5/1996 |
| JP | 2007-517122 A | 6/2007 |
| JP | 2012-44106 A | 3/2012 |
| JP | 2013-505309 A | 2/2013 |
| JP | 2013-133364 A | 7/2013 |
| JP | 2017-165882 A | 9/2017 |
| JP | 2017-197644 A | 11/2017 |
| WO | WO 2013/168717 A1 | 11/2013 |
| WO | WO 2016/158258 A1 | 10/2016 |

OTHER PUBLICATIONS

English Translation of Decision to Grant a Patent issued in Japanese Application No. 2018-228135, dated Apr. 3, 2019.
English Translation of Notice of Reasons for Refusal issued in Japanese Application No. 2018-228135, dated Jan. 7, 2019.
International Search Report (PCT/ISA/210) issued in PCT/JP2019/033854, dated Nov. 19, 2019.
Written Opinion of the International Searching Authority (PCT/ISA/237) issued in PCT/JP2019/033854, dated Nov. 19, 2019.

* cited by examiner

COMPOSITION, THERMOPLASTIC RESIN COMPOSITION CONTAINING THE SAME, AND MOLDED ARTICLE THEREOF

TECHNICAL FIELD

The present invention relates to a composition, a thermoplastic resin composition containing the same (hereinafter, also simply referred to as "resin composition"), and a molded article thereof. More particularly, the present invention relates to: a composition that has excellent fluidity and is capable of imparting excellent transparency and physical properties to thermoplastic resins; a thermoplastic resin composition containing the composition; and a molded article of the thermoplastic resin composition.

BACKGROUND ART

Thermoplastic resins, particularly olefin-based resins, such as polyethylene, polypropylene and polybutene-1, are inexpensive and have excellent properties in terms of moldability, hygiene, heat resistance, chemical resistance, mechanical characteristics, low specific gravity and the like; therefore, they have been widely utilized in a variety of molded articles, such as building materials, automobile materials, materials of household electric appliances and electronics, fiber materials, packaging materials, agricultural materials, housing materials of household electric appliances, household miscellaneous goods, medical equipment, food containers, beverage containers, films, sheets, and structural components.

However, olefin-based resins have drawbacks in that they have poor molding cycle characteristics due to their low post-molding crystallization rates, and that they are insufficient in terms of transparency and strength due to the generation of large crystals caused by the progress of crystallization after heat-molding. These drawbacks are all attributed to the crystallinity of olefin-based resins, and it is known that the above-described problems are solved by increasing the crystallization temperature of each olefin-based resin and thereby allowing the olefin-based resin to generate fine crystals rapidly.

It is known to add a nucleating agent for this purpose and, as the nucleating agent, for example, metal carboxylates, such as sodium benzoate, 4-tert-butylbenzoate aluminum salt, sodium adipate and 2-sodium-bicyclo[2.2.1]heptane-2,3-dicarboxylate; cyclic organophosphate metal salts, such as sodium-bis(4-tert-butylphenyl)phosphate, sodium-2,2'-methylene-bis(4,6-di-tert-butylphenyl)phosphate and lithium-2,2'-methylene-bis(4,6-di-tert-butylphenyl)phosphate; polyhydric alcohol derivatives, such as dibenzylidene sorbitol, bis(methylbenzylidene)sorbitol, bis(3,4-dimethylbenzylidene)sorbitol, bis(p-ethylbenzylidene)sorbitol and bis(dimethylbenzylidene)sorbitol; and amide compounds, such as N,N',N''-tris[2-methylcyclohexyl]-1,2,3-propane tricarboxamide, N,N',N''-tricyclohexyl-1,3,5-benzene tricarboxamide, N,N'-dicyclohexyl-naphthalene dicarboxamide and 1,3,5-tri(2,2-dimethylpropaneamide)benzene, are known.

Among these compounds, cyclic organophosphate metal salts are known as nucleating agents that have a large effect of improving the transparency and the physical properties of an olefin-based resin. For example, Patent Document 1 proposes a resin composition obtained by incorporating a basic aluminum salt of a cyclic organophosphate and sodium stearate into a crystalline synthetic resin. In addition, Patent Document 2 proposes a resin composition obtained by incorporating a basic multivalent metal salt of a cyclic organophosphate and an alkali metal carboxylate into a crystalline synthetic resin.

Further, Patent Document 3 describes that, as a nucleating agent, a mixture of one or more of sodium 2,2'-methylene-bis(4,6-di-tert-butylphenoxy)phosphate, sodium di(4-tert-butyl-phenoxy)phosphate, aluminum hydroxybis[2,2-methylene-bis(4,6-di-tert-butylphenoxy)phosphate], bis(2-alkyl, 4-alkylphenoxy)phosphate, sodium bicyclo[2,2,1]heptane dicarboxylate and calcium bicyclo[2,2,1]heptane dicarboxylate is preferred, and resin compositions in which this nucleating agent and sodium benzoate are added are described in the section of Examples. Moreover, Patent Document 4 proposes a composition obtained by mixing aluminum hydroxy p-tert-butylbenzoate and/or sodium benzoate with aluminum hydroxybis[2,2'-methylene-bis(4,6-di-tert-butylphenyl)phosphate]. Furthermore, Patent Document 5 proposes a polypropylene clarifying agent that contains a multivalent metal salt substituting a diaryl phosphoric acid and an alkali metal salt of a monobasic fatty acid.

RELATED ART DOCUMENTS

Patent Documents

[Patent Document 1] JPH08-120116A
[Patent Document 2] JPH 05-156078A
[Patent Document 3] CN102344609A
[Patent Document 4] CN101845171A
[Patent Document 5] CN101265347A

SUMMARY OF THE INVENTION

Problems to be Solved by the Invention

However, although combinations of aluminum hydroxybis[2,2'-methylene-bis(4,6-di-tert-butylphenyl)phosphate] and sodium stearate are described in Patent Documents 1 and 2, their nucleating effects are still insufficient, and a further improvement is thus demanded. In addition, although Patent Document 3 shows that the above-described resin compositions improve the creep resistance, incorporation of aluminum hydroxybis[2,2-methylene-bis(4,6-di-tert-butylphenyl)phosphate] is not examined therein, and the transparency and the physical properties are not adequately evaluated. Further, Patent Document 4 describes compositions obtained by blending sodium benzoate or a combination of sodium benzoate and aluminum hydroxy p-tert-hydroxy benzoate with aluminum hydroxybis[2,2-methylene-bis(4,6-di-tert-butylphenoxy)phosphate]; however, there is no further mention thereto and, since incorporation of these compositions into a resin is not evaluated, there is still room for investigation with regard to their effects on the transparency and the physical properties. Furthermore Patent Document 5 describes resin compositions that contain aluminum hydroxybis[2,2-methylene-bis(4,6-di-tert-butylphenoxy)phosphate], a sodium carboxylate such as sodium stearate or sodium rosinate, and/or an alkali metal salt of a monobasic fatty acid, such as lithium hydroxystearate; however, the effects of these resin compositions are not satisfactory, and a further improvement is thus demanded.

Moreover, aromatic phosphate metal salts have a drawback in that they exhibit poor fluidity as a powder and, therefore, it is demanded to improve the fluidity from the standpoints of transportability, workability, and measurability.

In view of the above, an object of the present invention is to provide: a composition that has excellent fluidity and is capable of imparting excellent transparency and physical properties to thermoplastic resins; a thermoplastic resin composition containing the composition; and a molded article of the thermoplastic resin composition.

Means for Solving the Problems

The present inventors intensively studied to solve the above-described problems and consequently discovered that the problems can be solved by adjusting the ratios of an aromatic phosphate metal salt, a sodium carboxylate, a fatty acid metal salt and a fatty acid to be in specific ranges, thereby completing the present invention.

That is, a composition of the present invention is a composition containing the below-described (A), (B), (C) and (D), the composition being characterized in that ratios of respective components with respect to a total amount of (A)+(B)+(C)+(D) are (A) 35 to 75% by mass, (B) 10 to 40% by mass, (C) 0 to 20% by mass, and (D) 5 to 35% by mass:

(A) an aromatic phosphate metal salt represented by the following Formula (1):

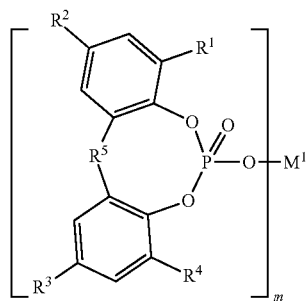

(1)

wherein, $R^1$ to $R^4$ each independently represent a hydrogen atom or a linear or branched alkyl group having 1 to 9 carbon atoms; $R^5$ represents an alkylidene group having 1 to 4 carbon atoms; m represents a number of 1 or 2; when m is 1, $M^1$ represents lithium; and when m is 2, $M^1$ represents hydroxyaluminum;

(B) a sodium carboxylate (C) a fatty acid metal salt represented by the following Formula (2):

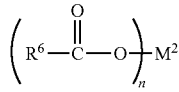

(2)

wherein, $R^6$ represents a group introduced to an aliphatic organic acid having 10 to 30 carbon atoms; $M^2$ represents an n-valent metal atom (provided that a sodium atom and a calcium atom are excluded) or $Al(OH)_{3-n}$; and n represents an integer of 1 to 3; and (D) a fatty acid.

In the composition of the present invention, the aromatic phosphate metal salt is preferably a compound represented by the following Formula (3):

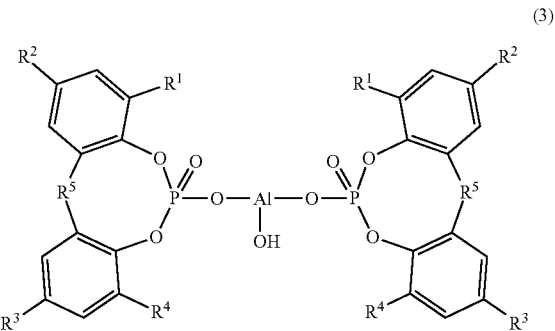

(3)

wherein, $R^1$ to $R^5$ have the same meanings as in Formula (1).

It is preferred that the composition of the present invention further contains at least one additive selected from the group consisting of a phenolic antioxidant, a phosphorus-based antioxidant, a thioether-based antioxidant, other antioxidant, a hindered amine compound, an ultraviolet absorber, a nucleating agent having a structure different from the one represented by Formula (1), a flame retardant, a flame retardant aid, a lubricant, a filler, a hydrotalcite, a fatty acid metal salt, an antistatic agent, a fluorescent brightener, a pigment, and a dye. In the composition of the present invention, it is also preferred that the (B) sodium carboxylate be a sodium aromatic carboxylate or a sodium-fatty acid. Further, in the composition of the present invention, it is preferred that the ratios of (A), (B), (C) and (D) are 35 to 55% by mass, 20 to 40% by mass, 5 to 20% by mass, and 5 to 35% by mass, respectively.

A thermoplastic resin composition of the present invention is characterized by containing the composition of the present invention such that the (A) aromatic phosphate metal salt represented by Formula (1) is incorporated in an amount of 0.001 to 10 parts by mass with respect to 100 parts by mass of a thermoplastic resin.

In the thermoplastic resin composition of the present invention, the thermoplastic resin is preferably an olefin-based resin, particularly a polypropylene.

A molded article of the present invention is characterized by containing the thermoplastic resin composition of the present invention.

Effects of the Invention

According to the present invention, a composition that has excellent fluidity and is capable of imparting excellent transparency and physical properties to thermoplastic resins, a thermoplastic resin composition containing the composition, and a molded article of the thermoplastic resin composition can be provided. Particularly, in the molded article of the present invention in which the composition of the present invention is used for a polypropylene, not only the transparency and the physical properties can be improved, but also the impact strength can be enhanced and coloration of the molded article can be suppressed.

MODE FOR CARRYING OUT THE INVENTION

Embodiments of the present invention will now be described in detail.

The composition of the present invention is a composition containing the below-described (A), (B), (C) and (D), in which the ratios of respective components with respect to a total amount of (A)+(B)+(C)+(D) are: (A) 35 to 75% by mass, (B) 10 to 40% by mass, (C) 0 to 20% by mass, and (D) 5 to 35% by mass. In this composition, (A) is an aromatic phosphate metal salt represented by the following Formula (1):

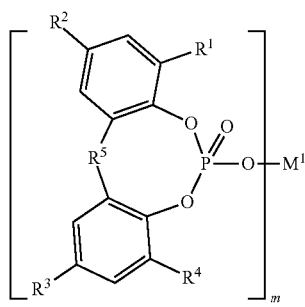

wherein, $R^1$ to $R^4$ each independently represent a hydrogen atom or a linear or branched alkyl group having 1 to 9 carbon atoms; $R^5$ represents an alkylidene group having 1 to 4 carbon atoms; m represents a number of 1 or 2; when m is 1, $M^1$ represents lithium; and when m is 2, $M^1$ represents hydroxyaluminum.

Further, (B) is a sodium carboxylate, and (C) is a fatty acid metal salt represented by the following Formula (2):

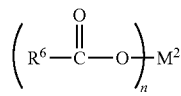

wherein, $R^6$ represents a group introduced to an aliphatic organic acid having 10 to 30 carbon atoms; $M^2$ represents an n-valent metal atom (provided that a sodium atom and a calcium atom are excluded) or $Al(OH)_{3-n}$; and n represents an integer of 1 to 3.

Moreover, (D) is a fatty acid.

First, the (A) aromatic phosphate metal salt represented by Formula (1) (hereinafter, also referred to as "component (A)") will be described. In Formula (1), $R^1$ to $R^4$ each independently represent a hydrogen atom or a linear or branched alkyl group having 1 to 9 carbon atoms; $R^5$ represents an alkylidene group having 1 to 4 carbon atoms; m represents a number of 1 or 2; when m is 1, $M^1$ represents lithium; and when m is 2, $M^1$ represents hydroxyaluminum.

Examples of the linear or branched alkyl group having 1 to 9 carbon atoms which is represented by $R^1$ to $R^4$ in the Formula (1) include a methyl group, an ethyl group, a propyl group, an isopropyl group, a butyl group, a sec-butyl group, a tert-butyl group, an isobutyl group, an amyl group, a tert-amyl group, a hexyl group, a heptyl group, an octyl group, an isooctyl group, a tert-octyl group, a 2-ethylhexyl group, a nonyl group and an isononyl group, among which a tert-butyl group is particularly preferred in the composition of the present invention.

Examples of the alkylidene group having 1 to 4 carbon atoms which is represented by $R^5$ in the Formula (1) include a methylene group, an ethylidene group, a propylidene group and a butylidene group, among which a methylene group is preferred in the composition of the present invention.

Examples of a method of producing the component (A) of the composition of the present invention include a method of allowing a cyclic phosphoric acid having a corresponding structure to react with a compound (e.g., a hydroxide, an oxide, a halide, a sulfate, a nitrate or an alkoxide compound of aluminum or lithium) using a reaction agent that is used as required, such as a basic compound; a method of allowing an alkali metal salt of an aromatic phosphate having a corresponding structure to undergo a salt exchange reaction with an aluminum compound (e.g., aluminum hydroxide, aluminum oxide, aluminum halide, aluminum sulfate, aluminum nitrate, or aluminum alkoxide compound) using a reaction agent that is used as required; and a method of generating a cyclic phosphoric acid by hydrolysis using cyclic phosphorus oxychloride as a starting substance and subsequently allowing the thus generated cyclic phosphoric acid to react with a metal compound.

Specific examples of the component (A) include the following compounds. It is noted here, however, that the composition of the present invention is not restricted thereto.

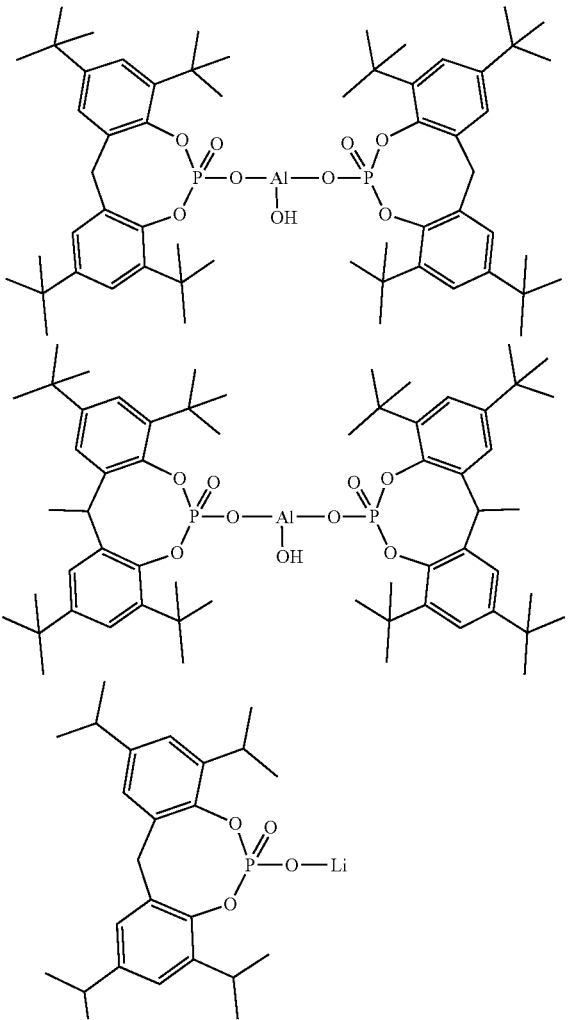

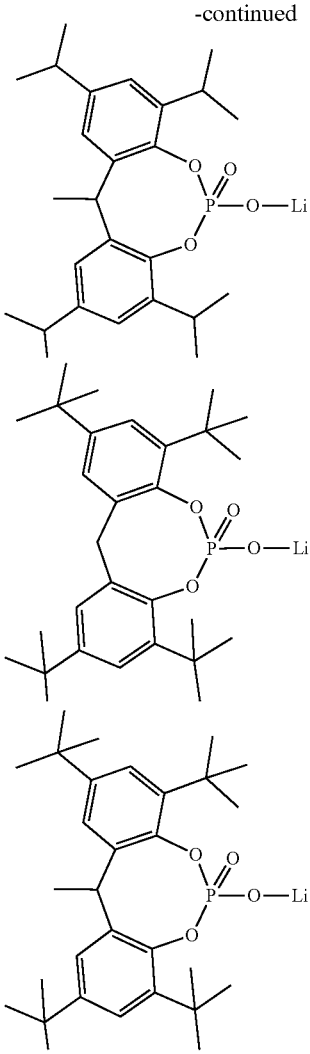

In the composition of the present invention, a compound represented by the following Formula (3) and lithium-2,2'-methylene-bis(4,6-di-tert-butylphenyl)phosphate are preferred as the component (A) since these compounds can impart good transparency and physical properties to thermoplastic resins:

(3)

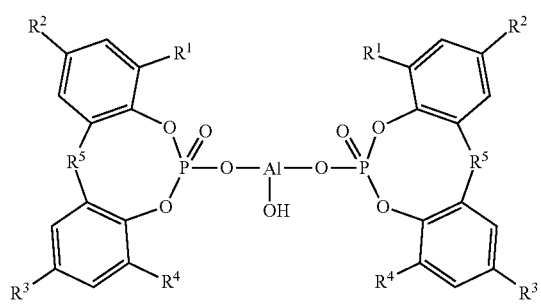

In the composition of the present invention, the compound (A) is not restricted in terms of the particle conditions such as particle size and particle size distribution; however, it is known that the smaller the particle size, the superior the dispersion in a resin, and the volume-average particle size of the compound (A) is preferably 100 μm or smaller, more preferably 30 μm or smaller, still more preferably 20 μm or smaller. The term "volume-average particle size" used herein refers to a volume-weighted average particle size determined by a laser diffraction-scattering particle size analyzer (MICROTRAC MT3000II, manufactured by MicrotracBEL Corp.).

In the composition of the present invention, the amount of the component (A) to be incorporated is in a range of 35 to 75% by mass, preferably 35 to 55% by mass, more preferably 38 to 50% by mass, with respect to a total amount of the components (A) to (D). When the amount of the component (A) is less than 35% by mass or greater than 75% by mass, not only the effects of the present invention are not attained, but also coloration of the resulting molded article may be increased.

The amount of the component (A) added to a thermoplastic resin is 0.001 to 10 parts by mass, preferably 0.006 to 5 parts by mass, with respect to 100 parts by mass of the thermoplastic resin. When the amount is less than 0.001 parts by mass, a nucleating effect may not be obtained, whereas an amount of greater than 10 parts by mass makes it difficult to disperse the component (A) into the thermoplastic resin, and the physical properties and the outer appearance of the resulting molded article is thereby adversely affected in some cases.

Next, the (B) sodium carboxylate (hereinafter, also referred to as "component (B)") will be described. The (B) sodium carboxylate is, for example, a sodium aromatic carboxylate or a sodium-fatty acid.

Examples of an aromatic carboxylic acid include benzoic acid, tert-butylbenzoic acid, methoxybenzoic acid, dimethoxybenzoic acid, trimethoxybenzoic acid, chlorobenzoic acid, dichlorobenzoic acid, trichlorobenzoic acid, acetoxybenzoic acid, biphenylcarboxylic acid, naphthalenecarboxylic acid, anthracenecarboxylic acid, furancarboxylic acid, and thenoic acid. In the composition of the present invention, the aromatic carboxylic acid is preferably benzoic acid or tert-butylbenzoic acid, since this makes the effects of the present invention prominent.

Examples of a fatty acid include an alkyl group or alkenyl group having 9 to 29 carbon atoms, and a fatty acid in which two or more unsaturated bonds are introduced, and a hydrogen atom of such a fatty acid may be substituted with a hydroxy group, and the fatty acid may have a branch as well. Specific examples of the fatty acid include saturated fatty acids, such as capric acid, 2-ethylhexanoic acid, undecylic acid, lauric acid, tridecylic acid, myristic acid, pentadecylic acid, palmitic acid, margaric acid, stearic acid, 12-hydroxystearic acid, nonadecylic acid, arachidic acid, heneicosylic acid, behenic acid, tricosylic acid, lignoceric acid, cerotic acid, montanoic acid, and melissic acid; and linear unsaturated fatty acids, such as 4-decenoic acid, 4-dodecenoic acid, palmitoleic acid, α-linolenic acid, linoleic acid, γ-linolenic acid, stearidonic acid, petroselinic acid, oleic acid, elaidic acid, vaccenic acid eicosapentaenoic acid, docosapentaenoic acid, and docosahexaenoic acid. In the composition of the present invention, a fatty acid having 10 to 21 carbon atoms is preferred, and a fatty acid having 12 to 18 carbon atoms is more preferred. Specifically, the fatty acid is particularly preferably lauric acid, myristic acid, palmitic acid, stearic acid, 12-hydroxystearic acid, oleic acid or linoleic acid, since this makes the effects of the present invention prominent.

In the composition of the present invention, the amount of the component (B) to be incorporated is in a range of 10 to 40% by mass, preferably 15 to 40% by mass, more preferably 20 to 40% by mass, still more preferably 22 to 35% by mass, with respect to a total amount of the components (A) to (D). When the amount of the component (B) is less than 10% by mass or greater than 40% by mass, the effects of the present invention may not be attained.

Next, the (C) fatty acid metal salt represented by Formula (2) (hereinafter, also referred to as "component (C)") will be described. In Formula (2), $R^6$ represents a group introduced to an aliphatic organic acid having 10 to 30 carbon atoms; $M^2$ represents an n-valent metal atom (provided that a sodium atom and a calcium atom are excluded) or $Al(OH)_{3-n}$; and n represents an integer of 1 to 3). Examples of the n-valent metal atom represented by $M^2$ include lithium, potassium, magnesium, barium, zinc, and aluminum. In the composition of the present invention, $M^2$ is preferably lithium, potassium, zinc, aluminum or hydroxyaluminum, more preferably lithium, potassium, or zinc.

In Formula (2), examples of the group introduced to an aliphatic organic acid having 10 to 30 carbon atoms, which group is represented by $R^6$, include alkyl groups, alkenyl groups and hydrocarbon groups in which two or more unsaturated bonds are introduced that have 9 to 29 carbon atoms. The alkyl groups and the alkenyl groups may be branched, and hydrogen atoms of the hydrocarbon groups may be substituted with hydroxy groups. Specific examples of the (C) fatty acid metal salt include lithium salts, potassium salts, magnesium salts, barium salts, zinc salts, aluminum salts and hydroxyaluminum salts of the fatty acids that are exemplified above for sodium carboxylate.

In the composition of the present invention, the fatty acid of the component (C) is preferably a fatty acid having 10 to 21 carbon atoms, more preferably a fatty acid having 12 to 18 carbon atoms. Specifically, the fatty acid of the component (C) is particularly preferably lauric acid, myristic acid, palmitic acid, stearic acid, 12-hydroxystearic acid, oleic acid or linoleic acid, since this makes the effects of the present invention prominent. In the composition of the present invention, as the component (C), a single compound may be used individually, or two or more compounds may be used in combination.

In the composition of the present invention, the amount of the component (C) to be incorporated is in a range of 0 to 20% by mass, preferably 5 to 20% by mass, more preferably 7 to 18% by mass, with respect to a total amount of the components (A) to (D). When this amount is greater than 20% by mass, the component (C) may bleed out of the resulting molded article.

Next, the (D) fatty acid (hereinafter, also referred to as "component (D)") will be described. In the composition of the present invention, examples of the (D) fatty acid include saturated fatty acids, such as butyric acid, valeric acid, caproic acid, enanthic acid, caprylic acid, pelargonic acid, 2-ethylhexanoic acid, capric acid, lauric acid, myristic acid, pentadecylic acid, palmitic acid, margaric acid, isostearic acid, stearic acid, 12-hydroxystearic acid, arachidic acid, heneicosylic acid, behenic acid, lignoceric acid, and montanoic acid; monounsaturated fatty acids, such as crotonic acid, myristoleic acid, palmitoleic acid, sapienic acid, oleic acid, elaidic acid, vaccenic acid, gadoleic acid, eicosenoic acid, erucic acid, and nervonic acid; diunsaturated fatty acids, such as linoleic acid, eicosadienoic acid, and docosadienoic acid; and unsaturated fatty acids having three or more unsaturated bonds, such as linolenic acid, pinolenic acid, eleostearic acid, mead acid, eicosatrienoic acid, stearidonic acid, arachidonic acid, eicosatetraenoic acid, adrenic acid, and docosahexaenoic acid.

In the composition of the present invention, the (D) fatty acid is preferably a fatty acid having 10 to 21 carbon atoms, more preferably a fatty acid having 12 to 18 carbon atoms. The (D) fatty acid is particularly preferably myristic acid, palmitic acid or stearic acid, since this makes the effects of the present invention prominent.

In the composition of the present invention, the amount of the component (D) to be incorporated is in a range of 5 to 35% by mass, preferably 7 to 28% by mass, with respect to a total amount of the components (A) to (D). When this amount is less than 5% by mass, the effects of the present invention may not be attained, whereas when the amount is greater than 35% by mass, the transparency may be reduced and coloration may be aggravated in the resulting molded article, and the component (D) may bleed out of the molded article.

In the composition of the present invention, other additives may be used within a range that does not impair the effects of the present invention. Examples thereof include a phenolic antioxidant, a phosphorus-based antioxidant, a thioether-based antioxidant, other antioxidant, a hindered amine compound, an ultraviolet absorber, a nucleating agent having a structure different from the one represented by Formula (1), a flame retardant, a flame retardant aid, a lubricant, a filler, a hydrotalcite, an antistatic agent, a fluorescent brightener, a pigment, and a dye. The amount of these other additives to be incorporated is not particularly restricted; however, it is preferably such an amount at which, when the composition of the present invention is blended into a thermoplastic resin, these other additives exist in the thermoplastic resin at an appropriate concentration.

Examples of the phenolic antioxidant include 2,6-di-tert-butyl-4-ethylphenol, 2-tert-butyl-4,6-dimethylphenol, styrenated phenol, 2,2'-methylene-bis(4-ethyl-6-tert-butylphenol), 2,2'-thiobis-(6-tert-butyl-4-methylphenol), 2,2'-thiodiethylene-bis[3-(3,5-di-tert-butyl-4-hydroxyphenyl) propionate], 2-methyl-4,6-bis(octylsulfanylmethyl)phenol, 2,2'-isobutylidene-bis(4,6-dimethylphenol), isooctyl-3-(3,5-di-tert-butyl-4-hydroxyphenyl)propionate, N,N'-hexane-1, 6-diylbis[3-(3,5-di-tert-butyl-4-hydroxyphenyl)propionamide], 2,2'-oxamide-bis[ethyl-3-(3,5-di-tert-butyl-4-hydroxyphenyl)propionate], 2-ethylhexyl-3-(3',5'-di-tert-butyl-4'-hydroxyphenyl)propionate, 2,2'-ethylene-bis(4,6-di-tert-butylphenol), esters of 3,5-di-tert-butyl-4-hydroxy-benzenepropanoic acid and a C13-15 alkyl, 2,5-di-tert-amylhydroquinone, hindered phenol polymers (e.g., trade name "AO.OH.98" manufactured by ADEKA Polymer Additives Europe SAS), 2,2'-methylene-bis[6-(1-methylcyclohexyl)-p-cresol], 2-tert-butyl-6-(3-tert-butyl-2-hydroxy-5-methylbenzyl)-4-methylphenyl acrylate, 2-[1-(2-hydroxy-3,5-di-tert-pentylphenyl)ethyl]-4,6-di-tert-pentylphenyl acrylate, 6-[3-(3-tert-butyl-4-hydroxy-5-methyl)propoxy]-2,4,8,10-tetra-tert-butylbenzo[d,f][1,3,2]-dioxaphosphepin, hexamethylene-bis[3-(3,5-di-tert-butyl-4-hydroxyphenyl) propionate, calcium bis[monoethyl(3,5-di-tert-butyl-4-hydroxybenzyl)phosphonate], a reaction product between 5,7-bis(1,1-dimethylethyl)-3-hydroxy-2(3H)-benzofuranone and o-xylene, 2,6-di-tert-butyl-4-(4,6-bis(octylthio)-1,3,5-triazine-2-ylamino)phenol, DL-α-tocophenol (vitamin E), 2,6-bis(α-methylbenzyl)-4-methylphenol, bis[3,3-bis-(4'-hydroxy-3'-tert-butyl-phenyl)butyric acid]glycol ester, 2,6-di-tert-butyl-p-cresol, 2,6-diphenyl-4-octadecyloxyphenol, stearyl(3,5-di-tert-butyl-4-hydroxyphenyl)propionate, distearyl(3,5-di-tert-butyl-4-hydroxybenzyl)phosphonate, tridecyl-3,5-tert-butyl-4-hydroxybenzyl thioacetate, thiodiethylene-bis[(3,5-di-tert-butyl-4-hydroxyphenyl)propionate], 4,4'-thiobis(6-tert-butyl-m-cresol), 2-octylthio-4,6-di(3,5- di-tert-butyl-4-hydroxyphenoxy)-s-triazine, 2,2'-methylene-bis(4-methyl-6-tert-butylphenol), bis[3,3-bis(4-hydroxy-3-tert-butylphenyl)butyric acid]glycol ester, 4,4'-butylidene-bis(2,6-di-tert-butylphenol), 4,4'-butylidene-bis(6-tert-butyl-3-methylphenol), 2,2'-ethylidene-bis(4,6-di-tert-butylphenol), 1,1,3-tris(2-methyl-4-hydroxy-5-tert-butylphenyl)butane, bis[2-tert-butyl-4-methyl-6-(2-hydroxy-3-tert-butyl-5-methylbenzyl)phenyl]terephthalate, 1,3,5-tris(2,6-dimethyl-3-hydroxy-4-tert-butylbenzyl)isocyanurate, 1,3,5-tris(3,5-di-tert-butyl-4-hydroxybenzyl)isocyanurate, 1,3,5-tris(3,5-di-tert-butyl-4-hydroxybenzyl)-2,4,6-trimethylbenzene, 1,3,5-tris[(3,5-di-tert-butyl-4-hydroxyphenyl)propionyloxyethyl]isocyanurate, tetrakis[methylene-3-(3',5'-tert-butyl-4'-hydroxyphenyl)propionate]methane, 2-tert-butyl-4-methyl-6-(2-acryloyloxy-3-tert-butyl-5-methylbenzyl)phenol, 3,9-bis[2-(3-tert-butyl-4-hydroxy-5-methylhydrocinnamoyloxy)-1,1-dimethylethyl]-2,4,8,10-tetraoxaspiro[5.5]undecane, triethylene glycol-bis[β-(3-tert-butyl-4-hydroxy-5-methylphenyl)propionate], and 3-(3,5-dialkyl-4-hydroxyphenyl)propionic acid derivatives, such as stearyl-3-(3,5-di-tert-butyl-4-hydroxyphenyl) propionic acid amide, palmityl-3-(3,5-di-tert-butyl-4-hydroxyphenyl)propionic acid amide, myristyl-3-(3,5-di-tert-butyl-4-hydroxyphenyl)propionic acid amide and lauryl-3-(3,5-di-tert-butyl-4-hydroxyphenyl)propionic acid amide. When a phenolic antioxidant is incorporated, the amount thereof is adjusted to be preferably 0.001 to 5 parts by mass, more preferably 0.03 to 3 parts by mass, with respect to 100 parts by mass of a thermoplastic resin.

Examples of the phosphorus-based antioxidant include triphenyl phosphite, diisooctyl phosphite, heptakis(dipropylene glycol)triphosphite, triisodecyl phosphite, diphenylisooctyl phosphite, diisooctylphenyl phosphite, diphenyltridecyl phosphite, triisooctyl phosphite, trilauryl phosphite, diphenyl phosphite, tris(dipropylene glycol) phosphite, dioleyl hydrogen phosphite, trilauryl trithiophosphite, bis(tridecyl)phosphite, tris(isodecyl)phosphite, tris(tridecyl)phosphite, diphenyldecyl phosphite, dinonylphenyl-bis(nonylphenyl)phosphite, poly(dipropylene glycol)phenyl phosphite, tetraphenyldipropyl glycol diphosphite, trisnonylphenyl phosphite, tris(2,4-di-tert-butylphenyl)phosphite, tris(2,4-di-tert-butyl-5-methylphenyl) phosphite, tris[2-tert-butyl-4-(3-tert-butyl-4-hydroxy-5-methylphenylthio)-5-methylphenyl]phosphite, tri(decyl) phosphite, octyldiphenyl phosphite, di(decyl)monophenyl phosphite, mixtures of distearyl pentaerythritol and calcium stearate, alkyl(C10) bisphenol-A phosphite, tetraphenyl-tetra(tridecyl)pentaerythritol tetraphosphite, bis(2,4-di-tert-butyl-6-methylphenyl)ethyl phosphite, tetra(tridecyl)isopropylidene diphenol diphosphite, tetra(tridecyl)-4,4'-n-butylidene-bis(2-tert-butyl-5-methylphenol)diphosphite, hexa(tridecyl)-1,1,3-tris(2-methyl-4-hydroxy-5-tert-butylphenyl)butane triphosphite, tetrakis(2,4-di-tert-butylphenyl) biphenylene diphosphonite, 9,10-dihydro-9-oxa-10-phosphaphenanthrene-10-oxide, (1-methyl-1-propanyl-3-ylidene) tris(1,1-dimethylethyl)-5-methyl-4,1-phenylene) hexatridecyl phosphite, 2,2'-methylene-bis(4,6-tert-butylphenyl)-2-ethylhexyl phosphite, 2,2'-methylene-bis(4,6-di-tert-butylphenyl)-octadecyl phosphite, 2,2'-ethylidene-bis(4,6-di-tert-butylphenyl)fluorophosphite, 4,4'-butylidene-bis(3-methyl-6-tert-butylphenylditridecyl) phosphite, tris(2-[(2,4,8,10-tetrakis-tert-butyldibenzo[d,f][1,3,2]dioxaphosphepin-6-yl)oxy]ethyl)amine, 3,9-bis(4-nonylphenoxy)-2,4,8,10-tetraoxa-3,9-diphosphaspiro[5,5] undecane, 2,4,6-tri-tert-butylphenyl-2-butyl-2-ethyl-1,3-propanediol phosphite, poly-4,4'-isopropylidene diphenol C12-15 alcohol phosphite, bis(diisodecyl)pentaerythritol diphosphite, bis(tridecyl)pentaerythritol diphosphite, bis(octadecyl)pentaerythritol diphosphite, bis(nonylphenyl)pentaerythritol diphosphite, bis(2,4-di-tert-butylphenyl)pentaerythritol diphosphite, bis(2,4,6-tri-tert-butylphenyl) pentaerythritol diphosphite, bis(2,6-di-tert-butyl-4-methylphenyl)pentaerythritol diphosphite, and bis(2,4-dicumylphenyl)pentaerythritol diphosphite. When a phosphorus-based antioxidant is incorporated, the amount thereof is adjusted to be preferably 0.001 to 10 parts by mass, more preferably 0.01 to 0.5 parts by mass, with respect to 100 parts by mass of a thermoplastic resin.

Examples of the thioether-based antioxidant include tetrakis[methylene-3-(laurylthio)propionate]methane, bis(methyl-4-[3-n-alkyl(C12/C14)thiopropionyloxy]-5-tert-butylphenyl)sulfide, ditridecyl-3,3'-thiodipropionate, dilauryl-3,3'-thiodipropionate, dimyristyl-3,3'-thiodipropionate, distearyl-3,3'-thiodipropionate, lauryl/stearyl thiodipropionate, 4,4'-thiobis(6-tert-butyl-m-cresol), 2,2'-thiobis(6-tert-butyl-p-cresol), and distearyl disulfide. When a thioether-based antioxidant is incorporated, the amount thereof is adjusted to be preferably 0.001 to 10 parts by mass, more preferably 0.01 to 0.5 parts by mass, with respect to 100 parts by mass of a thermoplastic resin.

Examples of the above-described other antioxidant include nitrone compounds, such as N-benzyl-α-phenyl nitrone, N-ethyl-α-methyl nitrone, N-octyl-α-heptyl nitrone, N-lauryl-α-undecyl nitrone, N-tetradecyl-α-tridecyl nitrone, N-hexadecyl-α-pentadecyl nitrone, N-octyl-α-heptadecyl nitrone, N-hexadecyl-α-heptadecyl nitrone, N-octadecyl-α-pentadecyl nitrone, N-heptadecyl-α-heptadecyl nitrone, and N-octadecyl-α-heptadecyl nitrone; and benzofuran compounds, such as 3-arylbenzofuran-2(3H)-one, 3-(alkoxyphenyl)benzofuran-2-one, 3-(acyloxyphenyl)benzofuran-2(3H)-one, 5,7-di-tert-butyl-3-(3,4-dimethylphenyl)-benzofuran-2(3H)-one, 5,7-di-tert-butyl-3-(4-hydroxyphenyl)-benzofuran-2(3H)-one, 5,7-di-tert-butyl-3-{4-(2-hydroxyethoxy)phenyl}-benzofuran-2(3H)-one, 6-(2-(4-(5,7-di-tert-2-oxo-2,3-dihydrobenzofuran-3-yl)phenoxy) ethoxy)-6-oxohexyl-6-((6-hydroxyhexanoyl)oxy) hexanoate, and 5-di-tert-butyl-3-(4-((15-hydroxy-3,6,9,13-tetraoxapentadecyl)oxy)phenyl)benzofuran-2(3H)-one.

When such other antioxidant is incorporated, the amount thereof is adjusted to be preferably 0.001 to 20 parts by mass, more preferably 0.01 to 5 parts by mass, with respect to 100 parts by mass of a thermoplastic resin.

Examples of the ultraviolet absorber include 2-hydroxybenzophenones, such as 2,4-dihydroxybenzophenone and 5,5'-methylene-bis(2-hydroxy-4-methoxybenzophenone); 2-(2-hydroxyphenyl)benzotriazoles, such as 2-(2-hydroxy-5-methylphenyl)benzotriazole, 2-(2-hydroxy-5-tert-octylphenyl) benzotriazole, 2-(2-hydroxy-3,5-di-tert-butylphenyl)-5-chlorobenzotriazole, 2-(2-hydroxy-3-tert-butyl-5-methylphenyl)-5-chlorobenzotriazole, 2-(2-hydroxy-3,5-dicumylphenyl)benzotriazole, 2,2'-methylene-bis(4-tert-octyl-6-benzotriazolylphenol), polyethylene glycol esters of 2-(2-hydroxy-3-tert-butyl-5-carboxyphenyl)benzotriazole, 2-[2-hydroxy-3-(2-acryloyloxyethyl)-5-methylphenyl]benzotriazole, 2-[2-hydroxy-3-(2-methacryloyloxyethyl)-5-tert-butylphenyl]benzotriazole, 2-[2-hydroxy-3-(2-methacryloyloxyethyl)-5-tert-octylphenyl]benzotriazole, 2-[2-hydroxy-3-(2-methacryloyloxyethyl)-5-tert-butylphenyl]-5-chlorobenzotriazole, 2-[2-hydroxy-5-(2-methacryloyloxyethyl)phenyl]benzotriazole, 2-[2-hydroxy-3-tert-butyl-5-(2-methacryloyloxyethyl)phenyl] benzotriazole, 2-[2-hydroxy-3-tert-amyl-5-(2-methacryloyloxyethyl)phenyl]benzotriazole, 2-[2-hydroxy-3-tert-butyl-5-(3-methacryloyloxypropyl)phenyl]-5- chlorobenzotriazole, 2-[2-hydroxy-4-(2-methacryloyloxymethyl)phenyl]benzotriazole, 2-[2-hydroxy-4-(3-methacryloyloxy-2-hydroxypropyl)phenyl]benzotriazole, and 2-[2-hydroxy-4-(3-methacryloyloxypropyl)phenyl]benzotriazole; benzoates, such as phenyl salicylate, resorcinol monobenzoate, 2,4-di-tert-butylphenyl-3,5-di-tert-butyl-4-hydroxybenzoate, octyl (3,5-di-tert-butyl-4-hydroxy)benzoate, dodecyl(3,5-di-tert-butyl-4-hydroxy)benzoate, tetradecyl(3,5-di-tert-butyl-4-hydroxy)benzoate, hexadecyl(3,5-di-tert-butyl-4-hydroxy) benzoate, octadecyl(3,5-di-tert-butyl-4-hydroxy)benzoate, and behenyl(3,5-di-tert-butyl-4-hydroxy)benzoate; substituted oxanilides, such as 2-ethyl-2'-ethoxyoxanilide and 2-ethoxy-4'-dodecyloxanilide; cyanoacrylates, such as ethyl-α-cyano-β,β-diphenylacrylate and methyl-2-cyano-3-methyl-3-(p-methoxyphenyl)acrylate; triazines, such as 2-(4,6-diphenyl-1,3,5-triazine-2-yl)-5-hexyloxyphenol, 2-(2-hydroxy-4-octoxyphenyl)-4,6-bis(2,4-dimethylphenyl)-1,3,5-triazine, trioctyl-2,2',2"-((1,3,5-triazine-2,4,6-triyl)tris(3-hydroxybenzene-4-,1-diyl)tripropionate), 2-(4,6-diphenyl-1,3,5-triazine-2-yl)-5-[2-(2-ethylhexanoyloxy)ethoxy]phenol, 2,4,6-tris(2-hydroxy-4-hexyloxy-3-methylphenyl)-1,3,5-triazine, and 1,12-bis[2-[4-(4,6-diphenyl-1,3,5-triazine-2-yl)-3-hydroxyphenoxy]ethyl] dodecane dioate; and a variety of metal salts and metal chelates, particularly salts and chelates of nickel and chromium. When an ultraviolet absorber is incorporated, the amount thereof is adjusted to be preferably 0.001 to 10 parts by mass, more preferably 0.01 to 0.5 parts by mass, with respect to 100 parts by mass of a thermoplastic resin.

Examples of the hindered amine compound include 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl)sebacate, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, bis(2,2,6,6-tetramethyl-4-piperidyl)-di(tridecyl)-1,2,3,4-butanetetracarboxylate, bis(1,2,2,6,6-pentamethyl-4-piperidyl)-di(tridecyl)-1,2,3,4-butanetetracarboxylate, bis(1,2,2,4,4-pentamethyl-4-piperidyl)-2-butyl-2-(3,5-di-tert-butyl-4-hydroxybenzyl)malonate, 1-(2-hydroxyethyl)-2,2,6,6-tetramethyl-4-piperidinol/diethylsuccinatepolycondensate, 1,6-bis(2,2,6,6-tetramethyl-4-piperidylamino)hexane/2,4-dichloro-6-morpholino-s-triazine polycondensate, 1,6-bis(2,2,6,6-tetramethyl-4-piperidylamino)hexane/2,4-dichloro-6-tert-octylamino-s-triazin e polycondensate, 1,5,8,12-tetrakis[2,4-bis(N-butyl-N-(2,2,6,6-tetramethyl-4-piperidyl)amino)-s-triazine-6-yl]-1,5,8,12-tetraazadodecane, 1,5,8,12-tetrakis[2,4-bis(N-butyl-N-(1,2,2,6,6-pentamethyl-4-piperidyl)amino)-s-triazine-6-yl]-1,5,8,12-tetraazadodecane, 1,6,11-tris[2,4-bis(N-butyl-N-(2,2,6,6-tetramethyl-4-piperidyl)amino)-s-triazine-6-yl]aminoundecane, 1,6,11-tris[2,4-bis(N-butyl-N-(1,2,2,6,6-pentamethyl-4-piperidyl)amino)-s-triazine-6-yl]amino undecane, bis{4-(1-octyloxy-2,2,6,6-tetramethyl)piperidyl}decanedionate, and bis{4-(2,2,6,6-tetramethyl-1-undecyloxy)piperidyl)carbonate. When a hindered amine compound is incorporated, the amount thereof is adjusted to be preferably 0.001 to 10 parts by mass, more preferably 0.01 to 0.5 parts by mass, with respect to 100 parts by mass of a thermoplastic resin.

Examples of the nucleating agent having a structure different from the one represented by Formula (1) include metal carboxylates, such as sodium benzoate, aluminum 4-tert-butylbenzoate, sodium adipate, and 2-sodium-bicyclo[2.2.1]heptane-2,3-dicarboxylate; polyol derivatives, such as dibenzylidene sorbitol, bis(methylbenzylidene)sorbitol, bis(3,4-dimethylbenzylidene)sorbitol, bis(p-ethylbenzylidene)sorbitol, and bis(dimethylbenzylidene)sorbitol; and amide compounds, such as N,N'N"-tris[2-methylcyclohexyl]-1,2,3-propane tricarboxamide, N,N',N"-tricyclohexyl-1,3,5-benzene tricarboxamide, N,N'-dicyclohexyl-naphthalene dicarboxamide, and 1,3,5-tri(dimethylisopropoylamino)benzene. When a nucleating agent having a structure different from the one represented by Formula (1) is incorporated, the amount thereof is adjusted to be preferably 0.03 to 10 parts by mass, more preferably 0.05 to 0.5 parts by mass, with respect to 100 parts by mass of a thermoplastic resin.

Examples of the flame retardant include aromatic phosphates, such as triphenyl phosphate, tricresyl phosphate, trixylenyl phosphate, cresyldiphenyl phosphate, cresyl-2,6-dixylenyl phosphate, resorcinol-bis(diphenylphosphate), (1-methylethylidene)-4,1-phenylene tetraphenyldiphosphate, and 1,3-phenylene-tetrakis(2,6-dimethylphenyl)phosphate, as well as "ADK STAB FP-500", "ADK STAB FP-600" and "ADK STAB FP-800" (trade names, manufactured by ADEKA Corporation); phosphonates, such as divinyl phenylphosphonate, diallyl phenylphosphonate, and (1-butenyl) phenylphosphonate; phosphinates, such as phenyl diphenylphosphinate, methyl diphenylphosphinate, and 9,10-dihydro-9-oxa-10-phosphaphenanthrene-10-oxide derivatives; phosphazene compounds, such as bis(2-allylphenoxy)phosphazene and dicresylphosphazene; phosphorus-based flame retardants, such as melamine phosphate, melamine pyrophosphate, melamine polyphosphate, melam polyphosphate, ammonium polyphosphate, piperazine phosphate, piperazine pyrophosphate, piperazine polyphosphate, phosphorus-containing vinylbenzyl compounds, and red phosphorus; metal hydroxides, such as magnesium hydroxide and aluminum hydroxide; and bromine-based flame retardants, such as brominated bisphenol A-type epoxy resins, brominated phenol novolac-type epoxy resins, hexabromobenzene, pentabromotoluene, ethylene-bis(pentabromophenyl), ethylene-bis-tetrabromophthalimide, 1,2-dibromo-4-(1,2-dibromoethyl)cyclohexane, tetrabromocyclooctane, hexabromocyclododecane, bis(tribromophenoxy)ethane, brominated polyphenylene ether, brominated polystyrene, 2,4,6-tris(tribromophenoxy)-1,3,5-triazine, tribromophenyl maleimide, tribromophenyl acrylate, tribromophenyl methacrylate, tetrabromobisphenol A-type dimethacrylate, pentabromobenzyl acrylate, and brominated styrene. These flame retardants are preferably used in combination with a drip inhibitor such as a fluorocarbon resin, and/or a flame retardant aid such as a polyhydric alcohol or hydrotalcite. When a flame retardant is incorporated, the amount thereof is adjusted to be preferably 1 to 100 parts by mass, more preferably 10 to 70 parts by mass, with respect to 100 parts by mass of a thermoplastic resin.

A lubricant is added for the purposes of imparting the surface of the resulting molded article with lubricity and improving the damage-preventing effect. Examples of the lubricant include unsaturated fatty acid amides, such as oleic acid amide and erucic acid amide; saturated fatty acid amides, such as behenic acid amide and stearic acid amide; butyl stearate; stearyl alcohols; stearic acid monoglyceride; sorbitan monopalmitate; sorbitan monostearate; mannitol; stearic acid; hardened castor oil; stearic acid amide; oleic acid amide; and ethylene-bis stearic acid amide. These lubricants may be used individually, or two or more thereof may be used in combination. When a lubricant is incorporated, the amount thereof is adjusted to be preferably 0.01 to 2 parts by mass, more preferably 0.03 to 0.5 parts by mass, with respect to 100 parts by mass of a thermoplastic resin.

Examples of the filler include talc, mica, calcium carbonate, calcium oxide, calcium hydroxide, magnesium carbonate, magnesium hydroxide, magnesium oxide, magnesium sulfate, aluminum hydroxide, barium sulfate, glass powder, glass fibers, clays, dolomite, mica, silica, alumina, potassium titanate whiskers, wollastonite, and fibrous magnesium oxysulfate, and any of these fillers can used by appropriately selecting the particle size (the fiber diameter, fiber length and aspect ratio in the case of a fibrous filler). Further, the filler to be used may be subjected to a surface treatment as required. When a filler is incorporated, the amount thereof is adjusted to be preferably 0.01 to 80 parts by mass, more preferably 1 to 50 parts by mass, with respect to 100 parts by mass of a thermoplastic resin.

The above-described hydrotalcite is a complex salt compound which is known as a natural or synthetic product and composed of magnesium, aluminum, hydroxy groups, a carbonate group and arbitrary crystal water, and examples thereof include hydrotalcites in which some of the magnesium or aluminum atoms are substituted with other metal such as an alkali metal or zinc; and hydrotalcites in which the hydroxyl group(s) and/or carbonate group is/are substituted with other anionic group(s), specifically hydrotalcites represented by the following Formula (4) in which a metal is substituted with an alkali metal. In addition, as an Al—Li hydrotalcite, a compound represented by the following Formula (5) can be used as well.

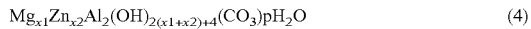

$$Mg_{x1}Zn_{x2}Al_2(OH)_{2(x1+x2)+4}(CO_3)pH_2O \quad (4)$$

wherein, x1 and x2 each represent a number that satisfies the conditions represented by the following equations; and p represents 0 or a positive number:

$$0 \le x2/x1 < 10,\ 2 \le (x1+x2) \le 20.$$

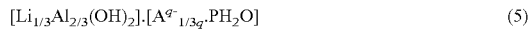

$$[Li_{1/3}Al_{2/3}(OH)_2] \cdot [A^{q-}{}_{1/3q} \cdot pH_2O] \quad (5)$$

wherein, $A^{q-}$ represents an anion having a valence of q; and p represents 0 or a positive number.

Further, the carbonate anion in these hydrotalcites may be partially substituted with other anion.

In these hydrotalcites, the crystal water may be dehydrated, and the hydrotalcites may be coated with, for example, a higher fatty acid such as stearic acid, a higher fatty acid metal salt such as alkali metal oleate, a metal organic sulfonate such as alkali metal dodecylbenzenesulfonate, a higher fatty acid amide, a higher fatty acid ester, or a wax.

The hydrotalcite may be a naturally-occurring or synthetic hydrotalcite. Examples of a synthesis method thereof include known methods that are described in JPS46-2280B1, JPS50-30039B1, JPS51-29129B1, JPH03-36839B2, JPS61-174270A, JPH5-179052A and the like. Further, the above-exemplified hydrotalcites can be used without any restriction in terms of crystal structure, crystal particles and the like. When a hydrotalcite is incorporated, the amount thereof is adjusted to be preferably 0.001 to 5 parts by mass, more preferably 0.01 to 3 parts by mass, with respect to 100 parts by mass of a thermoplastic resin.

Examples of the antistatic agent include cationic antistatic agents, such as fatty acid quaternary ammonium ion salts and polyamine quaternary salts; anionic antistatic agents, such as higher alcohol phosphates, higher alcohol EO adducts, polyethylene glycol fatty acid esters, anionic alkyl sulfonates, higher alcohol sulfates, higher alcohol ethylene oxide adduct sulfates, and higher alcohol ethylene oxide adduct phosphates; nonionic antistatic agents, such as polyhydric alcohol fatty acid esters, polyglycol phosphates, and polyoxyethylene alkyl allyl ethers; amphoteric antistatic agents, such as amphoteric alkyl betaines (e.g., alkyldimethylamino acetic acid betaines) and imidazoline-type amphoteric activators; and polymer-type antistatic agents, such as polyether ester amides. These antistatic agents may be used individually, or two or more thereof may be used in combination. When an antistatic agent is incorporated, the amount thereof is adjusted to be preferably 0.03 to 2 parts by mass, more preferably 0.1 to 0.8 parts by mass, with respect to 100 parts by mass of a thermoplastic resin.

As the above-described pigment, a commercially available pigment can be used as well, and examples thereof include PIGMENT RED 1, 2, 3, 9, 10, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, and 254; PIGMENT ORANGE 13, 31, 34, 36, 38, 43, 46, 48, 49, 51, 52, 55, 59, 60, 61, 62, 64, 65, and 71; PIGMENT YELLOW 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; PIGMENT GREEN 7, 10, and 36; PIGMENT BLUE 15, 15:1, 15:2, 15:3, 15:4, 15:5, 15:6, 22, 24, 29, 56, 60, 61, 62, and 64; and PIGMENT VIOLET 1, 15, 19, 23, 27, 29, 30, 32, 37, 40, and 50.

The fluorescent brightener is a compound which enhances the whiteness or blueness of a molded article by a fluorescent action of absorbing ultraviolet rays of solar light and artificial light, converting the absorbed ultraviolet rays into visible light of purple to blue and radiating the visible light. Examples of the fluorescent brightener include C.I. Fluorescent Brightener 184, which is a benzoxazole-based compound; C.I. Fluorescent Brightener 52, which is a coumarin-based compound; and C.I. Fluorescent Brighteners 24, 85 and 71, which are diaminostyrylbenzyl sulfone-based compounds. When a fluorescent brightener is incorporated, the amount thereof is adjusted to be preferably 0.00001 to 0.1 parts by mass, more preferably 0.00005 to 0.05 parts by mass, with respect to 100 parts by mass of a thermoplastic resin.

Examples of the dye include azo dyes, anthraquinone dyes, indigoid dyes, triarylmethane dyes, xanthene dyes, alizarin dyes, acridine dyes, stilbene dyes, thiazole dyes, naphthol dyes, quinoline dyes, nitro dyes, indamine dyes, oxazine dyes, phthalocyanine dyes and cyanine dyes, and a plurality of these dyes may be mixed and used in combination.

Next, the thermoplastic resin composition of the present invention will be described.

Resins that can be used in the thermoplastic resin composition of the present invention are not restricted as long as they are thermoplastic resins; however, from the standpoint of making the effects of the present invention prominent, a polyolefin-based resin, a styrene-based resin, a polyester-based resin, a polyether-based resin, a polycarbonate-based resin, a polyamide-based resin, or a halogen-containing resin is preferably used, and a polyolefin-based resin is more preferably used.

Examples of the polyolefin-based resin include α-olefin polymers, such as polyethylenes, low-density polyethylenes, linear low-density polyethylenes, high-density polyethylenes, cross-linked polyethylenes, ultrahigh-molecular-weight polyethylenes, polypropylenes, homopolypropylenes, random copolymer polypropylenes, block copolymer polypropylenes, isotactic polypropylenes, syndiotactic polypropylenes, hemi-isotactic polypropylenes, polybutenes, cycloolefin polymers, stereo block polypropylenes, poly-3-methyl-1-butenes, poly-3-methyl-1-pentenes, and poly-4-methyl-1-pentenes; α-olefin copolymers, such as ethylene-propylene block or random copolymers, impact copolymer polypropylenes, ethylene-methyl methacrylate copolymers, ethylene-methyl acrylate copolymers, ethylene-ethyl acrylate copolymers, ethylene-butyl acrylate copolymers, and ethylene-vinyl acetate copolymers; polyfluoroolefins; and polyolefin-based thermoplastic elastomers. The polyolefin-based resin may be a copolymer of two or more of these resins.

Examples of the styrene-based resin include vinyl group-containing aromatic hydrocarbon homopolymers, and copolymers of a vinyl group-containing aromatic hydrocarbon and other monomer(s) (e.g., maleic anhydride, phenylmaleimide, (meth)acrylate, butadiene and/or (meth)acrylonitrile), for example, thermoplastic resins such as polystyrene (PS) resins, high-impact polystyrenes (HIPS), acrylonitrile-styrene (AS) resins, acrylonitrile-butadiene-styrene (ABS) resins, methyl methacrylate-butadiene-styrene (MBS) resins, heat-resistant ABS resins, acrylate-styrene-acrylonitrile (ASA) resins, acrylonitrile-acrylic rubber-styrene (AAS) resins, styrene-maleic anhydride (SMA) resins, methacrylate-styrene (MS) resins, styrene-isoprene-styrene (SIS) resins, acrylonitrile-ethylene-propylene rubber-styrene (AES) resins, styrene-butadiene-butylene-styrene (SBBS) resins, and methyl methacrylate-acrylonitrile-butadiene-styrene (MABS) resins; and hydrogenated styrene-based elastomer resins obtained by hydrogenation of the double bond of butadiene or isoprene in any of the above-described resins, such as styrene-ethylene-butylene-styrene (SEBS) resins, styrene-ethylene-propylene-styrene (SEPS) resins, styrene-ethylene-propylene (SEP) resins, and styrene-ethylene-ethylene-propylene-styrene (SEEPS) resins.

Examples of the polyester-based resin include aromatic polyesters, such as polyalkylene terephthalates (e.g., polyethylene terephthalate, polybutylene terephthalate, and polycyclohexane dimethylene terephthalate) and polyalkylene naphthalates (e.g., polyethylene naphthalate and polybutylene naphthalate); linear polyesters such as polytetramethylene terephthalate; and degradable aliphatic polyesters, such as polyhydroxy butyrate, polycaprolactone, polybutylene succinate, polyethylene succinate, polylactic acid, polymalic acid, polyglycolic acid, polydioxane and poly(2-oxetanone).

Examples of the polyether-based resin include polyacetal, polyphenylene ether, polyether ketone, polyether ether ketone, polyether ketone ketone, polyether ether ketone ketone, polyether sulfone, and polyether imide.

Examples of the polycarbonate-based resin include polycarbonates, polycarbonate/ABS resins, polycarbonate/ASA resins, polycarbonate/AES resins, and branched polycarbonates.

Examples of the polyamide-based resin include polymers of ε-caprolactam (nylon 6), undecane lactam (nylon 11), lauryl lactam (nylon 12), aminocaproic acid, enantholactam, 7-aminoheptanoic acid, 11-aminoundecanoic acid, 9-aminononanoic acid, α-pyrrolidone, α-piperidone and the like; copolymers obtained by copolymerization of a diamine (e.g., hexamethylenediamine, nonanediamine, nonanemethylenediamine, methylpentadiamine, undecanemethylenediamine, dodecanemethylenediamine, or m-xylenediamine) and a carboxylic acid compound (e.g., a dicarboxylic acid such as adipic acid, sebacic acid, terephthalic acid, isophthalic acid, dodecanedicarboxylic acid, or glutaric acid); and mixtures of these polymers and/or copolymers.

Examples of the polyamide-based resin also include aramid resins such as "KEVLAR" (trade name) manufactured by DuPont, "NOMEX" (trade name) manufactured by DuPont, and "TWARON" (trade name) and "CONEX" (trade name) which are manufactured by TEIJIN Ltd.

Examples of the halogen-containing resin include polyvinyl chloride, polyvinylidene chloride, chlorinated polyethylene, chlorinated polypropylene, polyvinylidene fluoride, chlorinated rubbers, vinyl chloride-vinyl acetate copolymers, vinyl chloride-ethylene copolymers, vinyl chloride-vinylidene chloride copolymers, vinyl chloride-vinylidene chloride-vinyl acetate ternary copolymers, vinyl chloride-acrylate copolymers, vinyl chloride-maleate copolymers, and vinyl chloride-cyclohexylmaleimide copolymers.

Examples of the thermoplastic resin also include petroleum resins, coumarone resins, polyvinyl acetates, acrylic resins, polymethyl methacrylates, polyvinyl alcohols, polyvinyl formals, polyvinyl butyrals, polyphenylene sulfides, polyurethanes, cellulose-based resins, polyimide resins, polysulfones, liquid crystal polymers, and blends thereof.

Further, the thermoplastic resin may be an elastomer, such as an isoprene rubber, a butadiene rubber, an acrylonitrile-butadiene copolymer rubber, a styrene-butadiene copolymer rubber, a fluorocarbon rubber, a silicone rubber, a polyester-based elastomer, a nitrile-based elastomer, a nylon-based elastomer, a vinyl chloride-based elastomer, a polyamide-based elastomer or a polyurethane-based elastomer, or a combination of these elastomers.

In the resin composition of the present invention, these thermoplastic resins may be used individually, or two or more thereof may be used in combination. Further, these thermoplastic resins may be alloyed as well. These thermoplastic resins can be used regardless of, for example, molecular weight, polymerization degree, density, softening point, ratio of solvent-insoluble component(s), degree of stereoregularity, presence or absence of catalyst residue, type and blend ratio of each material monomer, and type of polymerization catalyst (e.g., a Ziegler catalyst or a metallocene catalyst).

In the thermoplastic resin composition of the present invention, a polyolefin-based resin is preferably used since it makes the effects of the present invention prominent.

A method of blending the composition of the present invention into a thermoplastic resin is not particularly restricted, and examples thereof include commonly-used methods, such as a method of dry-blending the thermoplastic resin in a powder or pellet form with the composition of the present invention, a method of preparing a masterbatch containing the composition of the present invention at a high concentration and subsequently adding the masterbatch to the thermoplastic resin, and a method of processing the composition of the present invention into a pellet form and subsequently adding the pellet to the thermoplastic resin.

As for a method of processing the composition of the present invention into a pellet form, a pellet can be produced by heating a mixture of the composition of the present invention, a phenolic antioxidant, a polymer compound, a binder such as a petroleum resin and, as required, other additive(s) to be optionally incorporated, and subsequently blending the mixture in the presence of the binder in a molten state. The processing conditions, the processing equipment and the like are not restricted at all, and any well-known and commonly-used processing method and processing equipment can be employed. Specific examples of the production method include a disk pelleter method and an extrusion method.

The thermoplastic resin composition of the present invention contains the composition of the present invention in a thermoplastic resin. As for the content of the composition of the present invention, the composition of the present invention is contained such that the aromatic phosphate metal salt represented by Formula (1) is incorporated in an amount of 0.001 to 10 parts by mass, preferably 0.01 to 0.5 parts by mass, with respect to 100 parts by mass of a thermoplastic resin. When this amount is less than 0.001 parts by mass, a transparency-improving effect may not be obtained, whereas when the amount is greater than 10 parts by mass, the composition of the present invention may bleed out of the resulting molded article and an effect of adding the composition may not be obtained, which is uneconomical.

In the thermoplastic resin composition of the present invention, an optional and known additive(s) (e.g., a phenolic antioxidant, a phosphorus-based antioxidant, a thioether-based antioxidant, other antioxidant, a hindered amine compound, an ultraviolet absorber, a nucleating agent, a flame retardant, a flame retardant aid, a lubricant, a filler, a hydrotalcite, an antistatic agent, a fluorescent brightener, a pigment, and a dye) may also be incorporated within a range that does not markedly impair the effects of the present invention. The amounts of the respective additives to be incorporated are, for example, as described above.

The resin composition of the present invention can be molded by any known molding method. A molded article can be obtained by, for example, injection molding, extrusion molding, blow molding, vacuum molding, inflation molding, calender molding, slush molding, dip molding, or foam molding.

Examples of the use of the resin composition of the present invention include automobile materials, such as bumpers, dash boards, and instrument panels; housing applications, such as refrigerators, laundry machines, and vacuum cleaners; household articles, such as tableware, buckets, and bath goods; miscellaneous goods, such as toys; molded articles, including storage/preservation containers such as tanks; films; and fibers.

EXAMPLES

The present invention will now be described more concretely by way of Examples thereof; however, the present invention is not restricted to the following Examples and the like by any means.

Examples 1-1 to 1-3 and Comparative Examples 1-1 to 1-3

To a homopolypropylene as a thermoplastic resin (melt flow rate: 8 g/10 min: 2.16 kg×230° C. according to ISO Standard 1133) in an amount of 100 parts by mass, 0.05 parts by mass of a phenolic antioxidant (tetrakis[methylene-3-(3', 5'-di-tert-butyl-4'-hydroxyphenyl)propionate]methane), 0.1 parts by mass of a phosphorus-based antioxidant (tris(2,4-di-tert-butylphenyl)phosphite), 0.05 parts by mass of calcium stearate and each composition shown in Table 1 were added, and these materials were mixed at 1,000 rpm for 1 minute using a Henschel mixer and subsequently granulated at an extrusion temperature of 230° C. using a biaxial extruder. The thus granulated pellets were each dried at 60° C. for 8 hours, after which the haze, the bending elastic modulus, the tensile elastic modulus, the Izod impact strength and the test piece yellowness (Y.I.) were measured under the below-described conditions. The results thereof are shown in Table 1 below. It is noted here that the unit of the amount of each component shown in Table 1 is parts by mass.

<Haze>

Using an injection molding machine (EC100-2A, manufactured by Toshiba Machine Co., Ltd.), the above-obtained pellets were each injection-molded at a resin temperature of 200° C. and a mold temperature of 50° C. to prepare test pieces. In Examples 1-1 to 1-3 and Comparative Examples 1-1 to 1-3, test pieces were prepared at dimensions of 60 mm×60 mm×2 mm. The test pieces were molded and, immediately thereafter, the resultants were left to stand in a 23° C. incubator for at least 48 hours, followed by measurement of the haze (%) using Haze Guard II (manufactured by BYK Additives & Instruments, Ltd.) in accordance with ISO14782.

<Bending Elastic Modulus (MPa)>

Using an injection molding machine (EC100-2A, manufactured by Toshiba Machine Co., Ltd.), the above-obtained pellets were each injection-molded at a resin temperature of 200° C. and a mold temperature of 50° C. to prepare test pieces having dimensions of 80 mm×10 mm×4 mm and, after leaving the thus obtained test pieces to stand for at least 48 hours in an incubator at 23° C., the bending elastic modulus (MPa) was measured in accordance with ISO178 using a bending tester "AG-IS" manufactured by Shimadzu Corporation.

<Tensile Elastic Modulus (MPa)>

Using an injection molding machine (EC100-2A, manufactured by Toshiba Machine Co., Ltd.), the above-obtained pellets were each injection-molded at a resin temperature of 200° C. and a mold temperature of 50° C. to prepare 1A-shaped dumbbell test pieces and, after leaving the thus obtained test pieces to stand for at least 48 hours in an incubator at 23° C., the tensile elastic modulus (MPa) was measured in accordance with ISO527-2 using a bending tester "AG-IS" manufactured by Shimadzu Corporation.

<Izod Impact Strength (kJ/m$^2$)>

Using an injection molding machine (EC100-2A, manufactured by Toshiba Machine Co., Ltd.), the above-obtained pellets were each injection-molded at a resin temperature of 200° C. and a mold temperature of 50° C. to prepare test pieces having dimensions of 80 mm×10 mm×4 mm and, after leaving the thus obtained test pieces to stand for at least 48 hours in an incubator at 23° C., the Izod impact strength (kJ/m$^2$) was measured in accordance with ISO180.

<Y.I.>

Using an injection molding machine (EC100-2A, manufactured by Toshiba Machine Co., Ltd.), the above-obtained pellets were each injection-molded at a resin temperature of 200° C. and a mold temperature of 50° C. to prepare test pieces having dimensions of 60 mm×60 mm×2 mm and, after leaving the thus obtained test pieces to stand for at least 48 hours in an incubator at 23° C., the Y.I. of each test piece was measured by a reflection method using "Multiple Light Source Spectrocolorimeter" manufactured by Suga Test Instruments Co., Ltd.

TABLE 1

|  | Example 1-1 | Example 1-2 | Example 1-3 | Comparative Example 1-1 | Comparative Example 1-2 | Comparative Example 1-3 |
|---|---|---|---|---|---|---|
| (A)-1 | 0.045 | 0.045 | 0.045 | — | 0.045 | 0.045 |
| (B)-1 | 0.028 | 0.028 | 0.028 | — | 0.028 | 0.028 |
| (C)-1 | 0.015 | 0.015 | 0.015 | — | 0.015 | 0.015 |
| (D)-1 | 0.005 | 0.012 | 0.030 | — | — | 0.050 |
| Total amount | 0.093 | 0.100 | 0.118 | — | 0.088 | 0.138 |
| Ratio of (A) [% mass] | 48.4 | 45 | 38.1 | — | 51.1 | 32.6 |
| Ratio of (B) [% mass] | 30.1 | 28 | 23.7 | — | 31.8 | 20.3 |
| Ratio of (C) [% mass] | 16.1 | 15 | 12.7 | — | 17.0 | 10.9 |
| Ratio of (D) [% by mass] | 5.3 | 12 | 25.4 | — | — | 36.2 |
| Haze (%)/2 mm | 61.0 | 61.6 | 62.7 | 86.4 | 60.0 | 64.1 |
| Bending elastic modulus (MPa) | 2,030 | 2,030 | 2,020 | 1,440 | 2,030 | 2,000 |
| Tensile elastic modulus (MPa) | 2,000 | 2,020 | 2,010 | 1,440 | 2,020 | 1,990 |
| Impact strength (kJ/m$^2$) | 3.60 | 3.68 | 3.56 | 3.36 | 3.35 | 3.70 |
| Improvement rate relative to impact strength of Comparative Example 1-1 (%) | 7.14 | 9.52 | 5.95 | 0 | −0.30 | 10.12 |
| Y.I. | 6.9 | 7.0 | 7.6 | 8.1 | 7.1 | 8.2 |

(A)-1: aluminum hydroxy bis[2,2'-methylene-bis(4,6-di-tert-butylphenyl)phosphate]
(B)-1: sodium benzoate
(C)-1: lithium myristate
(D)-1: stearic acid According to Comparative Examples 1-1 and 1-2, the molded articles not containing the (D) fatty acid did not exhibit an impact strength-improving effect. In addition, from Comparative Example 1-3, it was confirmed that, when the ratio of the (D) fatty acid with respect to the composition was greater than 30% by mass, the effect of improving the physical properties and the transparency were deteriorated, and the haze and coloration of the molded article were enhanced to deteriorate the external appearance.

On the other hand, from Examples 1-1 to 1-3, it was confirmed that the molded articles containing the composition of the present invention had an excellent balance of physical properties and transparency and exhibited excellent impact strength with hardly any coloration.

Examples 2-1 to 2-4 and Comparative Examples 2-1 and 2-2

For the compositions shown in Table 2 below, the rotating angle of repose and the degree of aggregation were evaluated by the below-described procedures. The composition of Example 2-4 was prepared based on the following formulation:
aluminum hydroxybis[2,2'-methylene-bis(4,6-di-tert-butylphenyl)phosphate]: 45% by mass,
sodium stearate: 28% by mass,
lithium myristate: 15% by mass, and
stearic acid: 12% by mass.

<Rotating Angle of Repose (°)>

The compositions shown in Table 2 were each added to a cylindrical container (500 mL) in a half volume of the cylindrical container, and this container was closed with a lid.

Subsequently, the fluidity of each sample was evaluated using a repose angle tester (Revolving Cylinder Test) manufactured by Tsutsui Scientific Instruments Co., Ltd. at a constant rotating speed of 2.4 rpm. As the cylindrical container rotates, the sample is piled up along the rotating container; however, the sample slides down from a high position. Once the slope formed by the sliding sample was constant, the angle formed by the slope of the sample and the horizontal plane was measured as the angle of repose. The results thereof are shown in Table 2.

<Degree of Aggregation (%)>

Each sample was classified using a powder characteristics analyzer (Multi Tester MT-02, manufactured by Seishin Enterprise Co., Ltd.) under the conditions of: opening of the sieve=355 μm (top sieve), 220 μm (middle sieve) and 150 μm (bottom sieve); sample weight=2 g; vibration amplitude=1 mm; vibration time=100 seconds, and a sum of the values of the following equations was defined as the degree of aggregation. The results thereof are shown in Table 2.

(Sample weight on top sieve/Total sample weight)× 100=Value of (a) (%)

(Sample weight on middle sieve/Total sample weight)×(3/5)×100=Value of (b) (%)

(Sample weight on bottom sieve/Total sample weight)×(1/5)×100=Value of (c) (%)

Degree of aggregation (%)=Value of (a) (%)+Value of (b) (%)+Value of (c) (%)

TABLE 2

|  | Example 2-1 | Example 2-2 | Example 2-3 | Example 2-4 | Comparative Example 2-1 | Comparative Example 2-2 |
|---|---|---|---|---|---|---|
| Composition | Composition of Example 1-1 | Composition of Example 1-2 | Composition of Example 1-3 | Composition of Example 2-4 | Composition of Comparative Example 1-2 | Composition of Comparative Example 1-3 |
| Rotating angle of repose (°) | 34.0 | 33.9 | 34.5 | 33.1 | 39.8 | 38.0 |
| Degree of aggregation (%) | 68.0 | 67.1 | 69.2 | 66.8 | 81.2 | 73.6 |

According to Comparative Example 2-1, the composition not containing the component (D) had a poor fluidity. Further, according to Comparative Example 2-2, the composition containing the component (D) at a ratio of greater than about 35% by mass also had a poor fluidity. On the other hand, from Examples 2-1 to 2-4, it was confirmed that the compositions according to the present invention, which contained the component (D) in a range of 3 to 35% by mass, had excellent fluidity.

Examples 3-1 to 3-15 and Comparative Examples 3-1 to 3-12

To a homopolypropylene as a thermoplastic resin (melt flow rate: 8 g/10 min; 2.16 kg×230° C. according to ISO Standard 1133) in an amount of 100 parts by mass, 0.05 parts by mass of a phenolic antioxidant (tetrakis[methylene-3-(3', 5'-di-tert-butyl-4'-hydroxyphenyl)propionate]methane), 0.1 parts by mass of a phosphorus-based antioxidant (tris(2,4-di-tert-butylphenyl)phosphite), 0.05 parts by mass of calcium stearate and each composition shown in Tables 3 to 6 were added, and these materials were mixed at 1,000 rpm for 1 minute using a Henschel mixer and subsequently granulated at an extrusion temperature of 230° C. using a biaxial extruder. It is noted here that, in Comparative Example 3-12, this granulation was performed without adding a composition. The granulated pellets were each dried at 60° C. for 8 hours, after which the crystallization temperature, the bending elastic modulus and the heat deflection temperature under load (HDT) were measured under the below-described conditions. The results thereof are shown in Tables 3 to 6 below. It is noted here that the unit of the amount of each component shown in these tables is parts by mass.

<Crystallization Temperature>

The crystallization temperature (° C.) was measured for each of the above-obtained pellets using a differential scanning calorimeter (DIAMOND, manufactured by PerkinElmer Co., Ltd.). As for the measurement method, in a chart obtained by heating each pellet from room temperature to 230° C. at a rate of 50° C./min, maintaining the pellet for 10 minutes and then cooling the pellet to 50° C. at a rate of −10° C./min, the temperature at which endothermic reaction formed a peak top was defined as the crystallization temperature (° C.).

<Bending Elastic Modulus (MPa)>

Using an injection molding machine (EC100-2A, manufactured by Toshiba Machine Co., Ltd.), the above-obtained pellets were each injection-molded at a resin temperature of 200° C. and a mold temperature of 50° C. to prepare test pieces having dimensions of 80 mm×10 mm×4 mm and, after leaving the thus obtained test pieces to stand for at least 48 hours in an incubator at 23° C., the bending elastic modulus (MPa) was measured in accordance with ISO178 using a bending tester "AG-IS" manufactured by Shimadzu Corporation.

<HDT>

Using an injection molding machine (EC100-2A, manufactured by Toshiba Machine Co., Ltd.), the above-obtained pellets were each injection-molded at a resin temperature of 200° C. and a mold temperature of 50° C. to prepare test pieces having dimensions of 80 mm×10 mm×4 mm and, after leaving the thus obtained test pieces to stand for at least 48 hours in an incubator at 23° C., the HDT (° C.) was measured in accordance with ISO75 using a HDT tester "AUTO HDT Tester 3A-2" manufactured by Toyo Seiki Seisaku-sho, Ltd.

TABLE 3

|  | Example 3-1 | Example 3-2 | Example 3-3 | Example 3-4 | Example 3-5 | Example 3-6 | Example 3-7 | Example 3-8 |
|---|---|---|---|---|---|---|---|---|
| (A)-1 | 0.035 | 0.040 | 0.040 | 0.040 | 0.050 | 0.050 | 0.055 | 0.055 |
| (A)-2 | — | — | — | — | — | — | — | — |
| (a)-1 | — | — | — | — | — | — | — | — |
| (B)-1 | 0.040 | 0.020 | 0.020 | 0.040 | 0.015 | 0.040 | 0.020 | 0.025 |
| (B)-2 | — | — | — | — | — | — | — | — |
| (b)-1 | — | — | — | — | — | — | — | — |
| (C)-1 | 0.015 | 0.005 | 0.020 | 0.010 | 0.015 | 0.005 | 0.005 | — |
| (C)-2 | — | — | — | — | — | — | — | — |
| (C)-3 | — | — | — | — | — | — | — | — |
| (C)-4 | — | — | — | — | — | — | — | — |
| (D)-1 | 0.010 | 0.035 | 0.020 | 0.010 | 0.020 | 0.005 | 0.020 | 0.020 |
| Total amount | 0.100 | 0.100 | 0.100 | 0.100 | 0.100 | 0.100 | 0.100 | 0.100 |
| Ratio of (A) [% by mass] | 35 | 40 | 40 | 40 | 50 | 50 | 55 | 55 |
| Ratio of (B) [% by mass] | 40 | 20 | 20 | 40 | 15 | 40 | 20 | 25 |

TABLE 3-continued

|  | Example 3-1 | Example 3-2 | Example 3-3 | Example 3-4 | Example 3-5 | Example 3-6 | Example 3-7 | Example 3-8 |
|---|---|---|---|---|---|---|---|---|
| Ratio of (C) [% by mass] | 15 | 5 | 20 | 10 | 15 | 5 | 5 | 0 |
| Ratio of (D) [% by mass] | 10 | 35 | 20 | 10 | 20 | 5 | 20 | 20 |
| Crystallization temperature (° C.) | 130.5 | 130.9 | 130.6 | 130.9 | 131.5 | 131.3 | 131.4 | 131.6 |
| Bending elastic modulus (MPa) | 1,900 | 1,890 | 1,900 | 1,910 | 1,910 | 1,910 | 1,900 | 1,900 |
| HDT (° C.) | 110.4 | 108.9 | 109.2 | 110.0 | 110.9 | 109.1 | 109.5 | 108.8 |

(A)-2: lithium (2,2'-methylene-bis(4,6-di-tert-butylphenyl)phosphate)
(B)-2: sodium stearate
(C)-2: zinc stearate
(C)-3: magnesium stearate
(C)-4: potassium stearate
(a)-1: sodium (2,2'-methylene-bis(4,6-di-tert-butylphenyl)phosphate)
(b)-1: potassium benzoate

TABLE 4

|  | Example 3-9 | Example 3-10 | Example 3-11 | Example 3-12 | Example 3-13 | Example 3-14 | Example 3-15 |
|---|---|---|---|---|---|---|---|
| (A)-1 | 0.060 | 0.075 | 0.045 | 0.040 | 0.040 | 0.040 | — |
| (A)-2 | — | — | — | — | — | — | 0.040 |
| (a)-1 | — | — | — | — | — | — | — |
| (B)-1 | 0.030 | 0.015 | — | 0.040 | 0.040 | 0.040 | 0.040 |
| (B)-2 | — | — | 0.025 | — | — | — | — |
| (b)-1 | — | — | — | — | — | — | — |
| (C)-1 | 0.005 | 0.005 | 0.020 | — | — | — | 0.010 |
| (C)-2 | — | — | — | 0.010 | — | — | — |
| (C)-3 | — | — | — | — | 0.010 | — | — |
| (C)-4 | — | — | — | — | — | 0.010 | — |
| (D)-1 | 0.005 | 0.005 | 0.010 | 0.010 | 0.010 | 0.010 | 0.010 |
| Total amount | 0.100 | 0.100 | 0.100 | 0.100 | 0.100 | 0.100 | 0.100 |
| Ratio of (A) [% by mass] | 60 | 75 | 45 | 40 | 40 | 40 | 40 |
| Ratio of (B) [% by mass] | 30 | 15 | 25 | 40 | 40 | 40 | 40 |
| Ratio of (C) [% by mass] | 5 | 5 | 20 | 10 | 10 | 10 | 10 |
| Ratio of (D) [% by mass] | 5 | 5 | 10 | 10 | 10 | 10 | 10 |
| Crystallization temperature (° C.) | 131.5 | 130.8 | 131.1 | 131.0 | 130.8 | 130.9 | 130.9 |
| Bending elastic modulus (MPa) | 1,910 | 1,910 | 1,920 | 1,900 | 1,890 | 1,890 | 1,890 |
| HDT (° C.) | 109.4 | 110.6 | 111.2 | 110.7 | 109.6 | 110.4 | 108.7 |

TABLE 5

|  | Comparative Example 3-1 | Comparative Example 3-2 | Comparative Example 3-3 | Comparative Example 3-4 | Comparative Example 3-5 | Comparative Example 3-6 |
|---|---|---|---|---|---|---|
| (A)-1 | 0.020 | 0.035 | 0.055 | 0.080 | 0.020 | — |
| (A)-2 | — | — | — | — | — | — |
| (a)-1 | — | — | — | — | — | 0.040 |
| (B)-1 | 0.045 | 0.010 | 0.005 | 0.010 | 0.020 | 0.040 |
| (B)-2 | — | — | — | — | — | — |
| (b)-1 | — | — | — | — | — | — |
| (C)-1 | 0.010 | 0.025 | 0.005 | 0.005 | 0.025 | 0.010 |
| (C)-2 | — | — | — | — | — | — |
| (C)-3 | — | — | — | — | — | — |

TABLE 5-continued

|  | Comparative Example 3-1 | Comparative Example 3-2 | Comparative Example 3-3 | Comparative Example 3-4 | Comparative Example 3-5 | Comparative Example 3-6 |
|---|---|---|---|---|---|---|
| (C)-4 | — | — | — | — | — | — |
| (D)-1 | 0.025 | 0.030 | 0.035 | 0.005 | 0.035 | 0.010 |
| Total amount | 0.100 | 0.100 | 0.100 | 0.100 | 0.100 | 0.100 |
| Ratio of (A) [% by mass] | 20 | 35 | 55 | 80 | 20 | (40) |
| Ratio of (B) [% by mass] | 45 | 10 | 5 | 10 | 20 | 40 |
| Ratio of (C) [% by mass] | 10 | 25 | 5 | 5 | 25 | 10 |
| Ratio of (D) [% by mass] | 25 | 30 | 35 | 5 | 35 | 10 |
| Crystallization temperature (° C.) | 130.2 | 130.2 | 130.0 | 129.5 | 130.2 | 130.3 |
| Bending elastic modulus (MPa) | 1,870 | 1,810 | 1,850 | 1,800 | 1,870 | 1,850 |
| HDT (° C.) | 107.3 | 104.3 | 106.7 | 103.0 | 108.1 | 107.6 |

TABLE 6

|  | Comparative Example 3-7 | Comparative Example 3-8 | Comparative Example 3-9 | Comparative Example 3-10 | Comparative Example 3-11 | Comparative Example 3-12 |
|---|---|---|---|---|---|---|
| (A)-1 | 0.040 | — | — | 0.060 | 0.100 | — |
| (A)-2 | — | — | — | — | — | — |
| (a)-1 | — | — | — | — | — | — |
| (B)-1 | — | 0.050 | 0.100 | — | — | — |
| (B)-2 | — | — | — | — | — | — |
| (b)-1 | 0.040 | — | — | — | — | — |
| (C)-1 | 0.010 | 0.020 | — | 0.020 | — | — |
| (C)-2 | — | — | — | — | — | — |
| (C)-3 | — | — | — | — | — | — |
| (C)-4 | — | — | — | — | — | — |
| (D)-1 | 0.010 | 0.030 | — | 0.020 | — | — |
| Total amount | 0.100 | 0.100 | 0.100 | 0.100 | 0.100 | — |
| Ratio of (A) [% by mass] | 40 | 0 | 0 | 60 | 100 | — |
| Ratio of (B) [% by mass] | (40) | 50 | 100 | 0 | 0 | — |
| Ratio of (C) [% by mass] | 10 | 20 | 0 | 20 | 0 | — |
| Ratio of (D) [% by mass] | 10 | 30 | 0 | 20 | 0 | — |
| Crystallization temperature (° C.) | 130.1 | 118.4 | 118.1 | 128.9 | 118.7 | 115.3 |
| Bending elastic modulus (MPa) | 1,860 | 1,640 | 1,540 | 1,850 | 1,450 | 1,440 |
| HDT (° C.) | 107.8 | 92.4 | 94.5 | 102.5 | 85.0 | 77.0 |

According to Comparative Examples 3-1 to 3-5, the compositions in which the formulation of (A), (B), (C) and (D) was outside the scope of the present invention exhibited a poor crystallization temperature-improving effect. In addition, according to Comparative Examples 3-6 and 3-7, none of the crystallization temperature, the bending elastic modulus and the HDT was satisfactory when the component (A) or the component (B) was different from that of the composition of the present invention. Moreover, according to Comparative Examples 3-8 to 3-11, the compositions not containing any one of the components (A), (B), (C) and (D) exhibited a poor effect in terms of improving the crystallization temperature and the bending elastic modulus.

In contrast, from Examples 3-1 to 3-15, it was confirmed that the composition of the present invention has a prominent effect of improving the crystallization temperature and is capable of yielding a molded article having excellent bending elastic modulus and HDT.

The invention claimed is:

1. A composition comprising the following (A), (B), (C) and (D), wherein ratios of respective components with respect to a total amount of (A)+(B)+(C)+(D) are
   (A) 35 to 75% by mass,
   (B) 10 to 40% by mass,
   (C) 0 to 20% by mass, and
   (D) 5 to 35% by mass:
   (A) an aromatic phosphate metal salt represented by the following Formula (1):

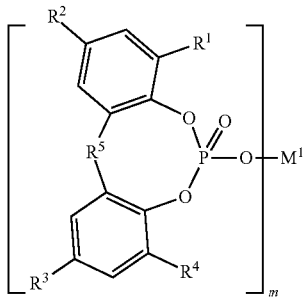

(1)

wherein, $R^1$ to $R^4$ each independently represent a hydrogen atom or a linear or branched alkyl group having 1 to 9 carbon atoms; $R^5$ represents an alkylidene group having 1 to 4 carbon atoms; m represents a number of 1 or 2; when m is 1, $M^1$ represents lithium; and when m is 2, $M^1$ represents hydroxyaluminum;

(B) a sodium carboxylate;
(C) a fatty acid metal salt represented by the following Formula (2):

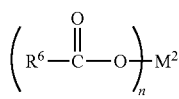

(2)

wherein, $R^6$ represents a group introduced to an aliphatic organic acid having 10 to 30 carbon atoms; $M^2$ represents an n-valent metal atom (provided that a sodium atom and a calcium atom are excluded) or $Al(OH)_{3-n}$; and n represents an integer of 1 to 3,
wherein calcium stearate is excluded from the (C) fatty acid metal salt; and
(D) a fatty acid.

2. The composition according to claim 1, wherein the aromatic phosphate metal salt is a compound represented by the following Formula (3):

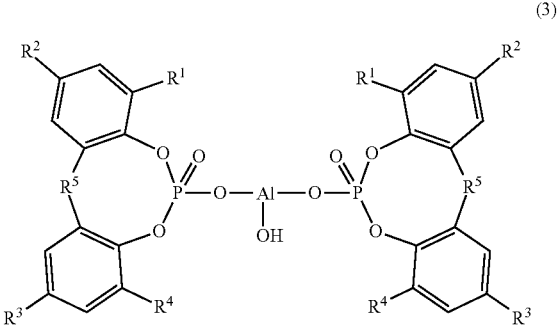

(3)

wherein, $R^1$ to $R^5$ have the same meanings as in Formula (1).

3. The composition according to claim 1, further comprising at least one additive selected from the group consisting of a phenolic antioxidant, a phosphorus-based antioxidant, a thioether-based antioxidant, other antioxidant, a hindered amine compound, an ultraviolet absorber, a nucleating agent having a structure different from the one represented by Formula (1), a flame retardant, a flame retardant aid, a lubricant, a filler, a hydrotalcite, an antistatic agent, a fluorescent brightener, a pigment, and a dye.

4. The composition according to claim 1, wherein the (B) sodium carboxylate is a sodium aromatic carboxylate or a sodium-fatty acid.

5. The composition according to claim 1, wherein the ratios of (A), (B), (C) and (D) are 35 to 55% by mass, 20 to 40% by mass, 5 to 20% by mass and 5 to 35% by mass, respectively.

6. The composition according to claim 1, wherein $M^2$ is lithium, potassium, magnesium, zinc, aluminum, or hydroxyaluminum.

7. A thermoplastic resin composition, comprising the composition according to claim 1 such that the (A) aromatic phosphate metal salt represented by Formula (1) is incorporated in an amount of 0.001 to 10 parts by mass with respect to 100 parts by mass of a thermoplastic resin.

8. The thermoplastic resin composition according to claim 7, wherein the thermoplastic resin is an olefin-based resin.

9. The thermoplastic resin composition according to claim 8, wherein the olefin-based resin is a polypropylene.

10. A molded article, comprising the thermoplastic resin composition according to claim 7.

* * * * *